United States Patent [19]

Hollenbeck

[11] Patent Number: 4,623,252

[45] Date of Patent: Nov. 18, 1986

[54] PARTICULATE COUNTER

[75] Inventor: Keith E. Hollenbeck, Mountain View, Calif.

[73] Assignee: Spectrex Corporation, Redwood City, Calif.

[21] Appl. No.: 658,770

[22] Filed: Oct. 9, 1984

[51] Int. Cl.[4] ............................................. G01N 15/02
[52] U.S. Cl. ..................................... 356/338; 356/427
[58] Field of Search ........................ 356/336, 338, 427

[56] References Cited

U.S. PATENT DOCUMENTS

| | | | |
|---|---|---|---|
| 3,858,851 | 1/1975 | Ogle | 356/336 |
| 3,956,616 | 5/1976 | Knollenberg | 235/92 |
| 4,011,459 | 3/1977 | Knollenberg et al. | 250/576 |

Primary Examiner—R. A. Rosenberger
Attorney, Agent, or Firm—A. C. Smith

[57] ABSTRACT

A particulate counter determines the size, number and distribution by size of various particles within a vessel by the principle of near angle scattering in which the portion of a light beam which is deflected by a given particle indicates detection and sizing of that particle. The counter disregards sidelobes which are caused by interference between the deflected portion of the beam and the beam itself by allowing only a single valid particle detection to occur in the space of a given time window.

14 Claims, 6 Drawing Figures

PARTICULATE COUNTER

BACKGROUND AND SUMMARY OF THE INVENTION

Particulate counters utilize the principle of near angle optical scattering to permit the counting and sizing of small particles contained within a sealed vessel. A portion of a light beam projected into the vessel is deflected by the presence of various moving particles within the beam. The scattered portion of the beam may be focused onto a photodiode and may be quantified so that a statistical analysis of the photodiode output waveform may be performed to yield an estimate of the distribution, number and size of the particles within the vessel.

Exemplary of particulate counters which are known in the prior art are those disclosed by Ogle in U.S. Pat. No. 3,858,851 and by Knollenberg in U.S. Pat. No. 3,956,616, both of which are incorporated herein by reference. Such prior art particulate counters determine the validity of individual particle detections by analyzing the amplitude and duration of each discrete pulse of the photodiode output waveform. Since it is assumed in the prior art that each pulse corresponds to a single detected particle, detection of a pulse which has an amplitude less than a threshhold amplitude or which has a pulse duration less than a threshhold duration indicates that only a partial detection has occurred. Similarly, detection of a pulse having a duration in excess of a maximum duration indicates that a particle out of the desired field of focus has been detected.

In accordance with the illustrated preferred embodiment of the present invention, a particulate counter selects as a valid particle detection only a single maximum photodiode waveform peak within a time window or sample period. Because of interference occurring between the main beam and the portion of the beam which is deflected by a given particle, the photodiode waveform caused by a valid particle detection may not be characterized as a single triangular pulse as is done in the prior art. Rather, the waveform may more accurately be characterized as a series of lobes contained within a pulse envelope. Thus, by counting each lobe as a discrete particle the prior art particle counters obtain an erroneous particle count. The particulate counter which is constructed in accordance with the illustrated preferred embodiment of the present invention selects only the single maximum peak within a time window or sample period as a valid particle detection and disregards the remaining lobes within the window. The durtion of the window may be chosen as the maximum time required for the relative movement of the beam across a stationary particle in order that multiple detections of the same particle may be disregarded.

DETAILED DESCRIPTION OF THE PREFERRED EMBODIMENT

Figure 1:
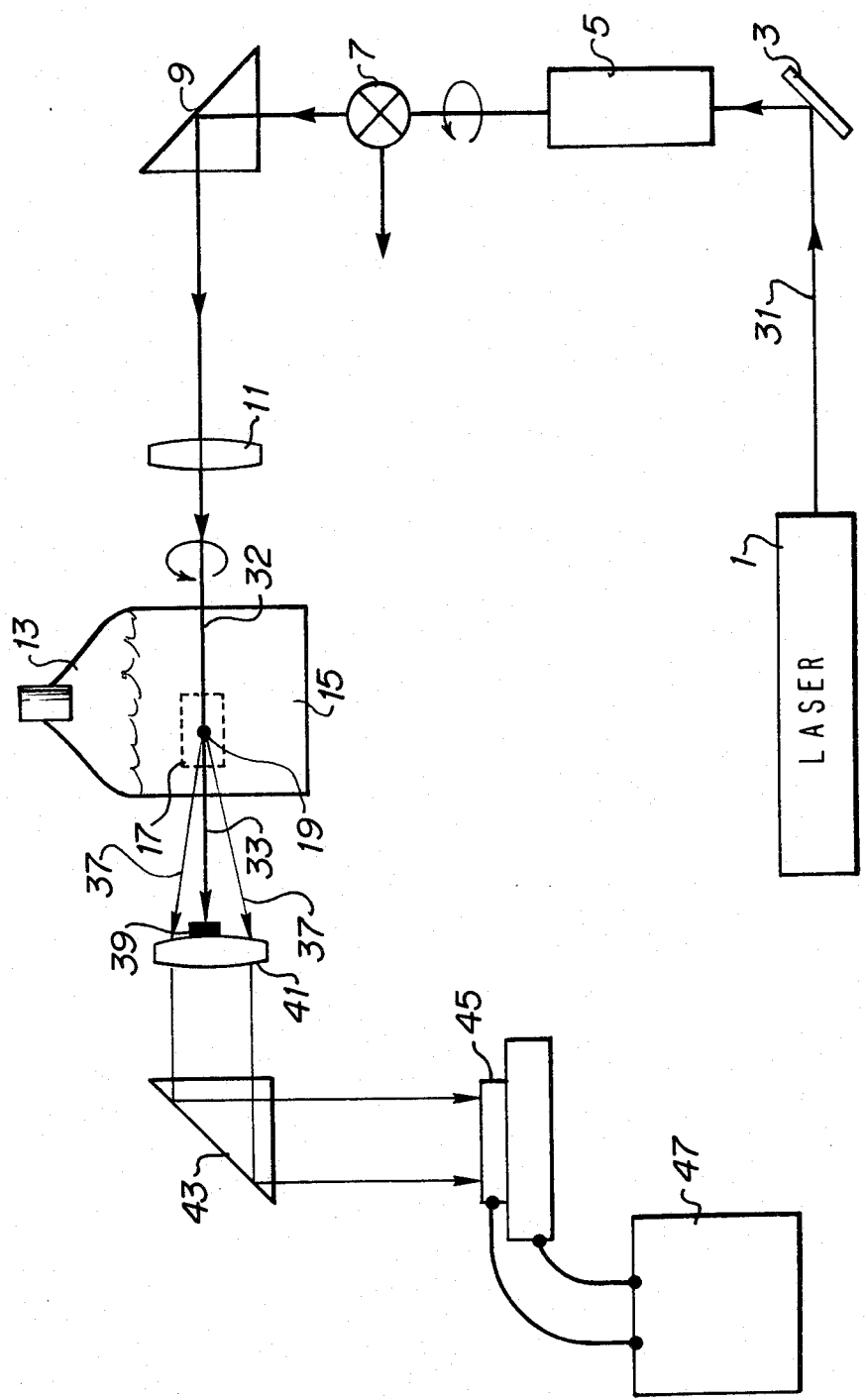
FIG. 1 shows a particulate counter which is constructed in accordance with the preferred embodiment of the present invention.

FIG. 1 shows a particulate counter which is constructed in accordance with the preferred embodiment of the present invention. A laser 1 generates a beam 31 which is used to detect the size, number and distribution of particles 19 contained in a fluid 15 within a vessel 13. Laser 1 may comprise any of a number of commercially available devices such as the Hughes Corp. model number 3221-H-PCS one milliwatt laser. Beam 31 is directed by a mirror 3 to a scanner 5 which rotates the beam in a circular pattern at a predetermined rate as shown in FIG. 1. Scanner 1 may easily be constructed by persons of ordinary skill in the art in accordance with the teachings of the above-referenced U.S. patents. A beam splitter 7 may be used to direct a portion of the beam 31 to a controller (not shown) which monitors and maintains the power of beam 31.

A prism 9 redirects beam 31 to a conventional primary lens 11 which focuses beam 31 on a sensitive zone or zone of detection 17 within vessel 13. The size of the detection zone 17 is determined both by the primary lens 11 and by a conventional secondary lens 41 and may be, e.g., 2 cm. long for a focused beam 31 having a diameter within zone 17 of 75 to 100 microns. Target 39 absorbs main beam 33 which is the undeflected portion of beam 31. Target 39 is 0.25 inch in diameter for a 0.125 inch diameter sweep of beam 31 caused by scanner 5. Secondary lens 41 focuses the deflected portion 37 of beam 31 through a prism 43 onto a photodiode 45. Detection circuit 47 analyzes the output of photodiode 45 to yield the estimated distribution, number and size of particles 19 contained within vessel 13.

Figure 2:
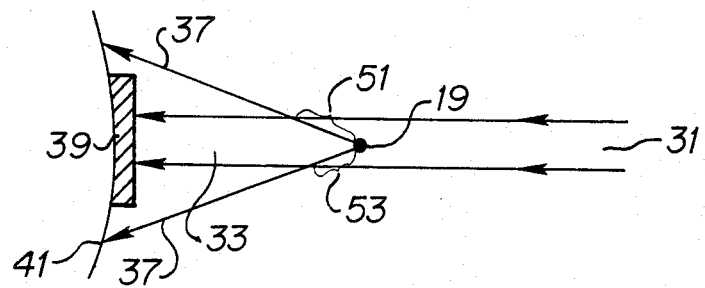
FIG. 2 shows a detailed view of beam scattering which occurs in the particulate counter shown in FIG. 1.

FIG. 2 shows a more detailed view of the deflection of beam 31 by particle 19. The particle 19 must have a diameter which is less than the diameter (e.g., 75 microns herein) of beam 31 within the detection zone 17 for an accurate particle detection to occur. The minimum detectable size of particle 19 is approximately the wavelength of beam 31, which is 630 nanometers for a typical HeNe laser 1. In operation, the contents of vessel 13 are gently agitated and beam 31 is scanned through a predetermined circular pattern within the detector zone 17. Of course, the fluid containing particles to be detected may also be moved laterally through the beam 31, or otherwise relative thereto, and as used herein, the term "scan" or "scanned" refers to the relative movement of the beam 31 with respect to a particle 19.

As beam 31 is scanned across particle 19, as shown in FIG. 2, beam portions 37 are deflected away from main beam 33 in accordance with the principle of near angle scattering. The amplitude of deflected portions 37 which bypass target 39 indicates the size of the particle 19. In regions 51 and 53 (which actually comprise a single cone when viewed in three dimensions) the deflected portion 37 must pass through the undeflected main beam 33. Because the distance traveled by portion 37 is greater than the distance traveled by beam 33, there exists a phase difference at each point of intersection. This, in turn, causes constructive and destructive interference to occur between the main beam 33 and the deflected portion 37.

Figure 3A:
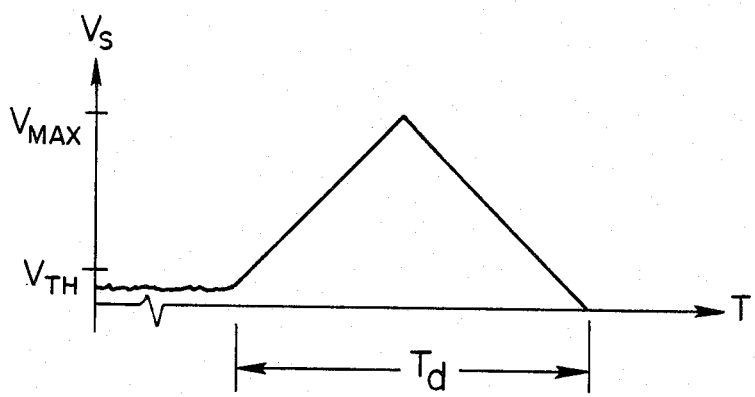
FIGS. 3A–B show the output waveform of the photodiode shown in FIG. 1.
Figure 3B:
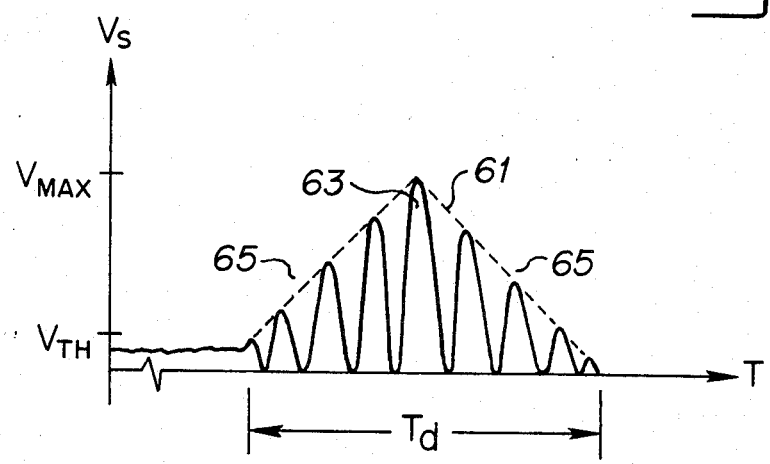

FIGS. 3A and 3B show the result of the interference which occurs between the main beam 33 and the deflected portion 37 as discussed above. If, as is assumed in the prior art, interference were not to occur as beam 31 scans across particle 19 in time $t_d$, then the output of photodiode 45 would be the triangle waveform shown in FIG. 3A. But, in fact, interference does occur and the true output of photodiode 45 is the lobe pattern shown in FIG. 3B. The actual waveform of FIG. 3B is limited by a triangular envelope 61 and is made up of a central lobe 63 having a maximum amplitude $V_{MAX}$ and various side lobes 65 having lesser amplitudes. The total duration of envelope 61 is the time $t_d$ which is required for beam 31 relatively to move entirely across a point starting when the sampled voltage $V_S$ exceeds a threshhold voltage $V_{TH}$. For the scan rate of the scanner 5 used in the particulate counter shown in FIG. 1, time $t_d$ is 10 ms.

Figure 4:
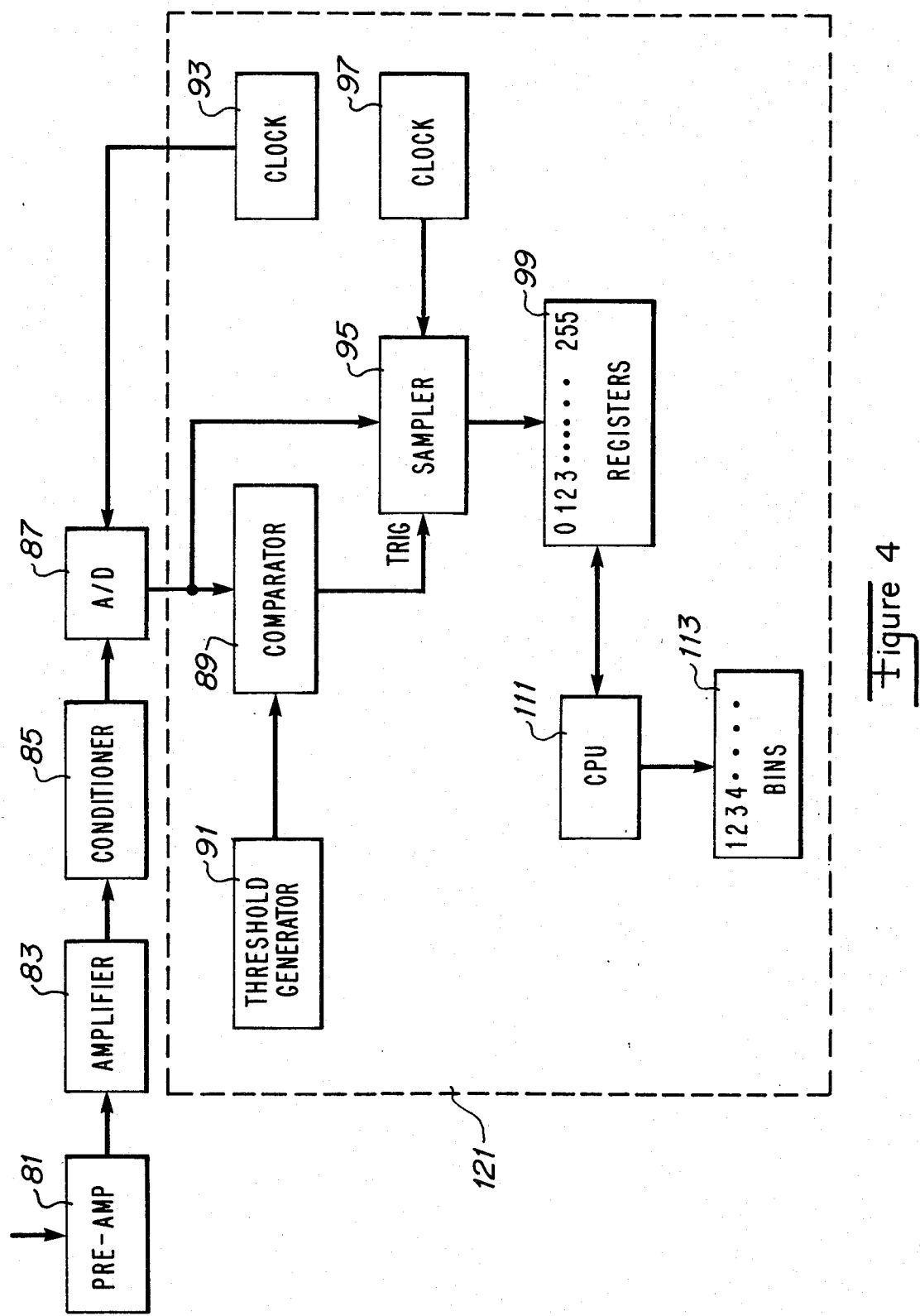
FIG. 4 is a block diagram of the detection circuit shown in FIG. 1.
Figure 5:
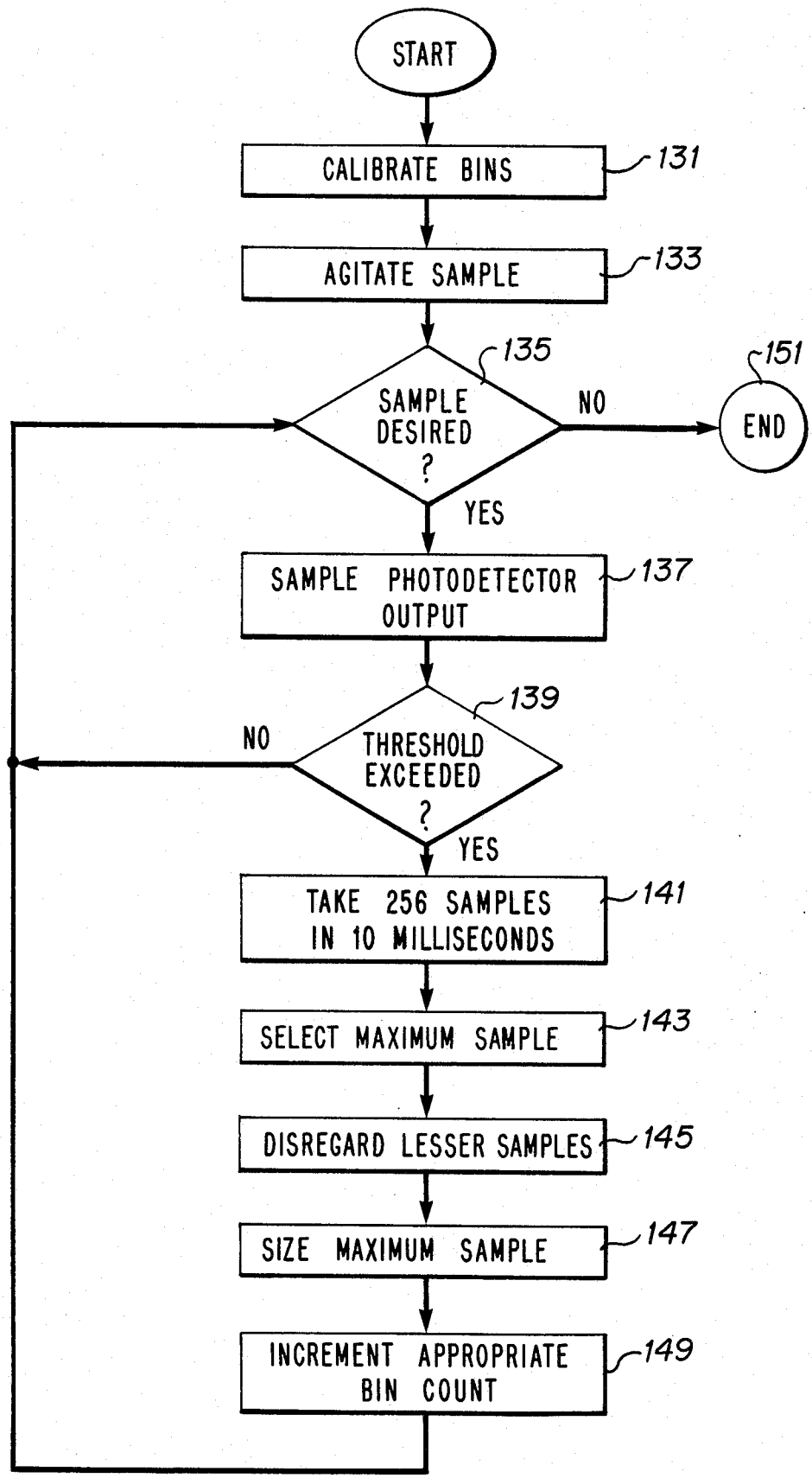
FIG. 5 is a flow chart of the steps performed by the particulate counter shown in FIG. 1.

FIG. 4 shows a block diagram of the detection circuit 47 shown in FIG. 1. Since each individual lobe contained within envelope 61 does not indicate a separate valid particle 19 detection it is necessary to limit the number of valid detections within time $t_d$ to one. FIG. 5 shows a block diagram of the method used by the particulate counter shown in FIG. 1 to accomplish this limitation using the components shown in the previous figures.

In step 131 of FIG. 5 various memory or storage bins 113, used to store the count of the various sizes of the detected particles 19, are calibrated for size. This calibration may be performed in accordance with any of a number of methods known to persons of ordinary skill in the art. In particular, the vessel 13 may be filled with a fluid 15 containing particulate matter having a known size distribution (such as A.C. Fine which is available from the Oklahoma State University at Stillwater). The particles 19 are detected by the particulate counter and the ranges of particle sizes associated with the memory bins 113 are adjusted until the detected size distribution matches the known distribution to a desired degree of accuracy. Each of the memory bins 113 may be viewed as storing the count of the number of detected particles within a predetermined range of amplitudes, $V_S$, and, thus, within a predetermined range of particle sizes.

In step 133, the vessel 13 is gently agitated and in step 135 the decision of whether or not to take a sample is made. The decision is based upon the total number of samples desired or the desired duration of the sampling period. Persons of ordinary skill in the art may easily make this determination in light of the scan rate of scanner 5 and in light of known methods for obtaining a statistically accurate estimate of the distribution, number and size of the particles 19.

If desired, a sample is taken in step 137. As shown in FIG. 4, pre-amplifier 81 and amplifier 83 amplify the output of the photodiode 45. A conditioner 85 may be used to filter or otherwise optimize the signal output of amplifier 83. An analog-to-digital converter 87, driven by a clock 93, converts the analog output of the conditioner 87 to a digital signal for futher processing. A comparator 89 then compares the digital signal to a threshhold level representing $V_{TH}$ generated by generator 91 to determine, in step 139, whether or not the digital signal represents a particle detection. If the threshhold level is exceeded then the comparator 89 triggers a sampler 95 to perform 256 samples of the output of the converter 87 in step 141. The sampler 95 operates at the clock rate of a clock 97 which is less than or equal to the clock rate of the clock 93. The clock rate of the clock 97 is set so that the 256 samples are performed in the time, $t_d$. The 256 samples are then stored in registers 99.

In steps 143 and 145, the one single maximum sample of the 256 samples is selected and the lesser samples are disregarded. This selection may be performed by a CPU 111 and the registers 99 (and also the memory bins 113) may comprise locations within a memory such as a RAM. In addition, component 121 shown in FIG. 4 may be any of a number of commercially available computers and associated memory such as the Apple Company model IIe. In step 147, the size of the maximum sample is determined and in step 149 the count contained within an appropriate one of memory bins 113 is incremented to indicate detection of a single particle of a particular size. Sizing may be performed by comparing the amplitude $V_{MAX}$ of the maximum sample to the voltage limits of the various ones of memory bins 113 which were determined in the calibration step 131 discussed above and which may have been stored in, e.g., a look-up table. The number stored in each of the memory bins 113 indicates that that number of particles within the predetermined size range associated with that memory bin were detected. Thus, the user is presented with the size, number and distribution of the particles 19 contained in the sample within vessel 13.

I claim:

1. An apparatus for detecting a particle within a vessel, comprising:
    light generation means for generating a light beam and for relatively moving the beam and a particle located in a detection zone within the vessel;
    detection means for receiving a scattered portion of the beam scattered by the particle and for generating a detection signal representing the scattered portion, and
    selection means, coupled to the detection means, for receiving the detection signal and for selecting a single maximum sample thereof occurring during a selected portion of the time period required for the particle to move through the light beam.

2. An apparatus as in claim 1, wherein the time period is substantially equal to a scan time required for the beam relatively to move across a point within the detection zone.

3. An apparatus as in claim 2, wherein the selection means comprises:
    threshold generator means for generating a threshold signal;
    comparator means, coupled to the detection means and to the threshold generator means, for issuing a trigger signal in response to the detection signal exceeding the threshold signal;
    sampling means, coupled to the comparator means and to the detection means, for taking a plurality of samples of the detection signal starting upon receiving the trigger signal and continuing for a sampling period substantially equal to the time period; and
    logic means, coupled to the sampling means, for receiving the samples from the sampling means and for selecting the single maximum sample therefrom.

4. An apparatus as in claim 3, further comprising storage means, coupled to the logic means, for receiving and storing the maximum sample.

5. An apparatus as in claim 4, wherein:

the storage means comprises a plurality of memory bins associated with selected different sample magnitudes;

the logic means is operative for selecting a particular memory bin corresponding to a magnitude of the maximum sample; and the logic means is further operative for demonstrating a count contained within the selected particular memory bin.

6. An apparatus as in claim 5, wherein the logic means comprises a computer.

7. An apparatus as in claim 6, wherein the light generation means comprises a laser.

8. An apparatus as in claim 1, wherein light generation means scans the beam through the detection zone within the vessel.

9. A method for detecting a particle within a vessel comprising the steps of:

generating a light beam;

relatively moving the light beam and a particle located in a detection zone within the vessel for scattering a portion of the beam that is intercepted by the particle;

detecting the scattered portion of the light beam; and selecting only a single maximum sample from the detected scattered portion within a time period.

10. A method as in claim 9, wherein the selected time period is substantially equal to a scan time required for the light beam relatively to move across a particle within the detection zone.

11. A method as in claim 10, wherein the step of selecting comprises:

triggering if the detected scattered portion exceeds a threshold value;

sampling the detected scattered portion after triggering occurs for a sampling period substantially equal to the selected time period; and determining the single maximum sample that occurred during the selected time period.

12. A method as in claim 11, further comprising the steps of:

comparing said maximum sample to a plurality of magnitude limits; storing counts of samples associated with selected magnitude limits; and incrementing the stored count associated with the mangitude of said maximum sample.

13. A method as in claim 12, wherein the magnitude of the maximum sample represents a size of the particle.

14. A method as in claim 9, wherein in the step of relatively moving the beam includes scanning the beam across a detection zone within the vessel.

* * * * *